(12) United States Patent
Kamishita et al.

(10) Patent No.: US 12,070,497 B2
(45) Date of Patent: Aug. 27, 2024

(54) HEPATITIS B VACCINE TRANSNASAL ADMINISTRATION SYSTEM

(71) Applicants: TOKO YAKUHIN KOGYO CO., LTD., Osaka (JP); NATIONAL UNIVERSITY CORPORATION EHIME UNIVERSITY, Matsuyama (JP); CENTRO DE INGENIERÍA GENÉTICA Y BIOTECNOLOGÍA, Ciudad de la Habana (CU)

(72) Inventors: Taizou Kamishita, Osaka (JP); Takashi Miyazaki, Osaka (JP); Yoichi Hiasa, Toon (JP); Fazle Akbar Sheikh Mohammad, Toon (JP); Osamu Yoshida, Toon (JP); Julio Cesar Aguilar Rubido, Ciudad de la Habana (CU); Gerardo Enrique Guillen Nieto, Ciudad de la Habana (CU); Eduardo Penton Arias, Ciudad de la Habana (CU)

(73) Assignees: TOKO YAKUHIN KOGYO CO., LTD., Osaka (JP); NATIONAL UNIVERSITY CORPORATION EHIME UNIVERSITY, Matsuyama (JP); CENTRO DE INGENIERÍA GENÉTICA Y BIOTECNOLOGÍA, Ciudad de la Habana (CU)

( * ) Notice: Subject to any disclaimer, the term of this patent is extended or adjusted under 35 U.S.C. 154(b) by 853 days.

(21) Appl. No.: 15/734,148

(22) PCT Filed: Jun. 4, 2019

(86) PCT No.: PCT/JP2019/022136
§ 371 (c)(1),
(2) Date: Dec. 1, 2020

(87) PCT Pub. No.: WO2019/235466
PCT Pub. Date: Dec. 12, 2019

(65) Prior Publication Data
US 2021/0187101 A1 Jun. 24, 2021

(30) Foreign Application Priority Data
Jun. 5, 2018 (JP) .................. 2018-107797

(51) Int. Cl.
C12N 5/00 (2006.01)
A61K 9/12 (2006.01)
A61K 39/12 (2006.01)
A61K 39/29 (2006.01)
A61K 47/32 (2006.01)

(52) U.S. Cl.
CPC ............. *A61K 39/29* (2013.01); *A61K 9/12* (2013.01); *A61K 47/32* (2013.01)

(58) Field of Classification Search
None
See application file for complete search history.

(56) References Cited

U.S. PATENT DOCUMENTS

| 7,374,766 | B1 | 5/2008 | Aguilar Rubido et al. |
|---|---|---|---|
| 11,638,791 | B2* | 5/2023 | Yabe ............... B05B 11/02 |
| | | | 604/218 |
| 2003/0072764 | A1 | 4/2003 | O'Hagan |
| 2003/0180351 | A1 | 9/2003 | Gluck et al. |
| 2009/0275668 | A1 | 11/2009 | Kamishita |
| 2009/0306341 | A1 | 12/2009 | Emmert |
| 2012/0082697 | A1 | 4/2012 | Hasegawa et al. |
| 2017/0128363 | A1 | 5/2017 | Kamshita et al. |
| 2017/0128364 | A1 | 5/2017 | Kamshita et al. |

FOREIGN PATENT DOCUMENTS

| CN | 1332637 A | 1/2002 |
|---|---|---|
| EP | 2014305 | 1/2009 |
| EP | 3162378 | 5/2017 |
| JP | 2002-529427 | 9/2002 |
| JP | 2004-527524 | 9/2004 |
| JP | 2016-007409 | 1/2016 |
| RU | 2603729 C2 | 11/2016 |
| WO | 2000/32229 A1 | 6/2000 |
| WO | 2007/012319 | 2/2007 |
| WO | 2010/114169 | 10/2010 |

OTHER PUBLICATIONS

Aguilar at al. (Immunology and Cell Biology, 2004, vol. 82, p. 539-546).*
Saito et al. (Vaccine, 2016, p. 1201-1207).*
Office Action issued for Russian Patent Application No. 2020142983, Nov. 17, 2022, 11 pages including English.
JC Aguilar et al., "Development of a nasal vaccine for chronic hepatitis B infection that uses the ability of hepatitis B core antigen to stimulate a strong Th1 response against hepatitis B surface antigen", Immunology and Cell Biology, 2004, vol. 82, pp. 539-546.
"NASVAC Phase-III Trial in Chronic Hepatitis B (CHB) Patients (NASVAC)", ClinicalTrials.gov, Dec. 11, 2012, NCT01374308, 6 pages.
Mamun Al-Mahtab et al., "Therapeutic potential of a combined hepatitis B virus surface and core antigen vaccine in patients with chronic hepatitis B", Hepatology International, 2013, vol. 7, No. 4, pp. 981-989.
Abe M et al. "Immunotherapy for chronic hepatitis due to HBV", Japanese Journal of Clinical Medicine, 2011, vol. 69, No. 4, pp. 503-506; A concise explanation of relevance provided in the attached International Search report.
International Search Report of PCT/JP2019/022136, Sep. 3, 2019, 2 pages.

(Continued)

*Primary Examiner* — Agnieszka Boesen
(74) *Attorney, Agent, or Firm* — HSML P.C.

(57) ABSTRACT

The present invention relates to a rhinovaccination system for preventing and treating hepatitis B, comprising a hepatitis B vaccine composition for administration to nasal mucosa in combination with a medical nozzle device.

16 Claims, 7 Drawing Sheets

(56) References Cited

OTHER PUBLICATIONS

International Preliminary Report on Patentability of PCT/JP2019/022136, Dec. 8, 2020, 6 pages.

Bum-Gil Kim et al., "Evaluation of the effects of biodegradable nanoparticles on a vaccine delivery system using AFM, SEM, and TEM," Ultramicroscopy, Elsevier, Amsterdam, NL, vol. 108, No. 10, Sep. 1, 2008, pp. 1168-1173, XP024100782.

Tetsuya Oka et al., "Influenza vaccine: enhancement of immune response by application of carboxy-vinylpolymer," Vaccine, Elsevier, Amsterdam, NL, vol. 8, No. 6, Dec. 1, 1990, pp. 573-576, XP026927094.

The extended European search report issued for European Patent Application No. 19816086.3, Feb. 9, 2022, 9 pages.

Mamun-Al-Mahtab et al., "Topic: 8 Hepatitis B—Clinical Absno:LB8, Phase III study of a therapeutic vaccine candidate (NASVAC) containing the hepatitis B virus core antigen (HBcAg) and the HBV surface antigen (HBsAg) for treatment of patients with chronic hepatitis B," Hepatol Int, 2014, vol. 8, S398-S399; Available at: https://link.springer.com/article/10.1007/s12072-014-9519-7.

Office Action issued on Nov. 4, 2023 in Chinese patent application No. 201980035576.2, 8 pages.

Office Action issued on Nov. 21, 2023 in Japanese patent application No. 2020-523114, 10 pages with machine translation.

\* cited by examiner (a)

(b)

| Size (μm) | % V < | % V | Size (μm) | % V < | % V | Size (μm) | % V < | % V |
|---|---|---|---|---|---|---|---|---|
| 0.117 | 0.00 | 0.00 | 2.51 | 0.00 | 0.00 | 54.12 | 50.14 | 10.61 |
| 0.136 | 0.00 | 0.00 | 2.93 | 0.00 | 0.00 | 63.10 | 61.14 | 10.99 |
| 0.158 | 0.00 | 0.00 | 3.41 | 0.00 | 0.00 | 73.56 | 71.76 | 10.62 |
| 0.185 | 0.00 | 0.00 | 3.98 | 0.00 | 0.00 | 85.77 | 81.23 | 9.47 |
| 0.215 | 0.00 | 0.00 | 4.64 | 0.00 | 0.00 | 100.00 | 88.93 | 7.70 |
| 0.251 | 0.00 | 0.00 | 5.41 | 0.00 | 0.00 | 116.59 | 94.52 | 5.58 |
| 0.293 | 0.00 | 0.00 | 6.31 | 0.00 | 0.00 | 135.94 | 97.98 | 3.46 |
| 0.341 | 0.00 | 0.00 | 7.36 | 0.00 | 0.00 | 158.49 | 99.64 | 1.66 |
| 0.398 | 0.00 | 0.00 | 8.58 | 0.01 | 0.01 | 184.79 | 100.00 | 0.36 |
| 0.464 | 0.00 | 0.00 | 10.00 | 0.09 | 0.08 | 215.44 | 100.00 | 0.00 |
| 0.541 | 0.00 | 0.00 | 11.66 | 0.34 | 0.24 | 251.19 | 100.00 | 0.00 |
| 0.631 | 0.00 | 0.00 | 13.59 | 0.87 | 0.53 | 292.87 | 100.00 | 0.00 |
| 0.736 | 0.00 | 0.00 | 15.85 | 1.86 | 0.99 | 341.46 | 100.00 | 0.00 |
| 0.858 | 0.00 | 0.00 | 18.48 | 3.53 | 1.67 | 398.11 | 100.00 | 0.00 |
| 1.00 | 0.00 | 0.00 | 21.54 | 6.12 | 2.58 | 464.16 | 100.00 | 0.00 |
| 1.17 | 0.00 | 0.00 | 25.12 | 9.87 | 3.75 | 541.17 | 100.00 | 0.00 |
| 1.36 | 0.00 | 0.00 | 29.29 | 15.01 | 5.14 | 630.96 | 100.00 | 0.00 |
| 1.58 | 0.00 | 0.00 | 34.15 | 21.68 | 6.68 | 735.64 | 100.00 | 0.00 |
| 1.85 | 0.00 | 0.00 | 39.81 | 29.91 | 8.23 | 857.70 | 100.00 | 0.00 |
| 2.15 | 0.00 | 0.00 | 46.42 | 39.53 | 9.62 | 1000.00 | 100.00 | 0.00 |

| Title | Average | σ | Min | Max |
|---|---|---|---|---|
| Trans (%) | 85.3 | 0.2229 | 84.6 | 85.8 |
| Dv(10) (μm) | 25.23 | 0.6506 | 23.96 | 26.79 |
| Dv(50) (μm) | 54.01 | 1.11 | 51.61 | 56.48 |
| Dv(90) (μm) | 102.6 | 2.117 | 97.97 | 107 |
| Span | 1.432 | 0.02509 | 1.334 | 1.494 |
| Dv(0) (μm) | 8.205 | 2.667 | 1.023 | 9.641 |
| D[4][3] (μm) | 59.67 | 1.185 | 57.17 | 62.23 |
| D[3][2] (μm) | 44.85 | 1.373 | 40.2 | 46.73 |
| Cv (PPM) | 66.66 | 2.731 | 55.5 | 70.72 |
| %V < 10μ (%) | 0.09299 | 0.1679 | 0.01111 | 0.614 |
| 10μ < %V < 100μ (%) | 88.84 | 0.8771 | 86.89 | 90.77 |
| 100μ < %V < 200μ (%) | 11.07 | 0.8914 | 9.172 | 12.97 |
| %V > 200μ (%) | 0 | 0 | 0 | 0 |

HEPATITIS B VACCINE TRANSNASAL ADMINISTRATION SYSTEM

TECHNICAL FIELD

The present invention relates to a rhinovaccination system to administer a hepatitis B vaccine composition to nasal mucosa for preventing and treating hepatitis B, which is used in combination with a medical nozzle device.

BACKGROUND ART

Hepatitis B is a hepatitis caused by infection with hepatitis B virus (HBV), which gets infected through blood or body fluid. The persistent infection of HBV to hepatocyte can cause chronic hepatitis, hepatic cirrhosis, hepatocellular carcinoma.

The treatment of chronic hepatitis B (CHB) is now carried out mainly by using interferon preparation (IFN) or nucleoside analog preparation (NA) as first-line therapy. In IFN therapy, some effective examples have been reported which increase immunity to sustain the growth inhibition of virus effectively, but in general, IFN therapy has low HBV clearance rate and strong side effect which has been a big problem. On the other hand, NA therapy has a high HBV clearance rate of about 95%, but the therapeutic effect is temporary and it cannot bring in complete cure. Thus, it is necessary to accept the administration over a lifetime. Accordingly, NA therapy also has big problems of compliance and medical economy, and the emergence of drug-resistant virus after long-term use has been also reported. Therefore a new therapy for CHB has been desired.

The approved Hepatitis B vaccine in Japan is only a way that HBs antigen (hepatitis B surface antigen) of hepatitis B virus is administered subcutaneously or intramuscularly, which has attained some good results in major reduction of HBV carriers. For the treatment of CHB, the immunotherapy with HBV vaccine has been also tried in the past, but it has not been sufficiently successful in the treatment.

For the above problem of hepatitis B vaccination, a wide variety of the trials have been done until now, in which a vaccine for nasal administration has received attention as a new hepatitis B vaccination. However, it has been reported that it is impossible to induce a high immune response to hepatitis B virus and bring in a sufficient therapeutic effect, even though the vaccine for subcutaneous or intramuscular vaccination which has been broadly used in current clinical practice is nasally administered to experimental animals or human beings directly.

In the course of time, the Center for Genetic Engineering and Biotechnology (CIGB) in Cuba has developed a nasal vaccine for the treatment of hepatitis B which comprises two kinds antigens, HBs antigen and HBc antigen, and then has succeeded in commercialization of product as a trade name: HeberNasvac (non-Patent Reference 1), after clinical testing in Bangladesh. In the administration method thereof, however, it is required to be used in conjunction with subcutaneous vaccination to gain a sufficient immune response, i.e., it is a two-cycle vaccination, not a complete vaccine for administration to nasal mucosa.

As mentioned above, it has been desired to develop hepatitis B vaccine for nasal administration as a next-generation hepatitis B vaccination and put it to practical use, which can take the place of a conventional hepatitis B vaccine for subcutaneous or intramuscular administration. However, any effective hepatitis B vaccination for nasal administration has not been found. That is, there are various problems for the practical use.

PRIOR ART

[Patent Reference 1] WO 2010/114169
[Patent Reference 2] WO 2007/012319

SUMMARY OF INVENTION

Technical Problem

One of the purposes of the present invention is to provide a system to administer a hepatitis B vaccine which is used in combination with an administration device, which is expected to completely cure hepatitis B.

Solution to Problem

The present inventors have extensively studied on the above problem and then have found that a combination of (i) a gel base (material) for spray-administration to nasal mucosa comprising carboxy vinyl polymer which is treated by adding an outside shearing force to add spray-performance and (ii) HBs antigen and HBc antigen, can enhance the immune induction in human beings without an adjuvant; and further have made an administration system by setting the above combination into a metered-dose syringe-based squirt having an optimized shape/configuration of the nozzle, which can increase the antibody titer for hepatitis B virus to give an excellent therapy effect for hepatitis B. Based upon the new findings, the present invention has been accomplished. The present invention may provide the following embodiments.

[1] A rhinovaccination system of hepatitis B vaccine, comprising a syringe-based squirt filled with a hepatitis B vaccine composition which comprises (i) hepatitis B surface antigen (HBs antigen) and/or hepatitis B nucleocapsid antigen (HBc antigen), and (ii) a gel base material comprising carboxy vinyl polymer which is treated by adding an outside shearing force to add spray-performance.

[2] The rhinovaccination system of hepatitis B vaccine according to [1], wherein the syringe-based squirt is a medical syringe having a tip opening in fluid communication with a syringe barrel, which is equipped with a rhinal spray nozzle comprising
 a hollow nozzle body having a tip portion defining a nozzle orifice thereon,
 a solid packing rod arranged within the nozzle body, and
 a nozzle chamber defined between the packing rod and the nozzle body to allow a fluid communication between the tip opening and the nozzle orifice,
 wherein the nozzle orifice has a diameter in a range between 0.25 mm and 0.30 mm.

[3] The rhinovaccination system of hepatitis B vaccine according to [1] or [2], wherein the amount of (i) the hepatitis B vaccine is 0.01-10 mg/mL per each antigen.

[4] The rhinovaccination system of hepatitis B vaccine according to any one of [1] to [3], wherein the hepatitis B vaccine composition comprises 0.1 w/v % to 1.0 w/v % carboxy vinyl polymer.

[5] The rhinovaccination system of hepatitis B vaccine according to any one of [1] to [4], wherein the spray-performance is to control (1) the particle-size-distribution of the sprayed composition, (2) the uniformity of spray density, and/or (3) the spray angle.

[6] The rhinovaccination system of hepatitis B vaccine according to any one of [1] to [3], wherein the hepatitis B vaccine composition is prepared by treating a gel base material comprising 0.5 w/v % to 2.0 w/v % carboxy vinyl polymer by adding an outside shearing force to control (1) the particle-size-distribution of the sprayed composition, (2) the uniformity of spray density, and/or (3) the spray angle, as spray-performance, to give a gel base material, and then
    mixing the resulting gel base material with a virus stock solution comprising hepatitis B surface antigen (HBs antigen) and/or hepatitis B nucleocapsid antigen (HBc antigen) homogeneously in a short time without stress.

[7] The rhinovaccination system of hepatitis B vaccine according to any one of [1] to [6], wherein the hepatitis B vaccine composition is prepared with a gel base material comprising carboxy vinyl polymer that is treated by adding an outside shearing force to add spray-performance which is to control that (1) as for the particle-size-distribution of the sprayed composition, the mean particle size is in a range of 30 μm to 80 μm, and the particle distribution between 10 μm and 100 μm is 80% or more,
    (2) the spray density is uniform to form a homogeneous full-cone shape, and
    (3) the spray angle is adjusted in a range of 30° to 70°.

[8] The rhinovaccination system of hepatitis B vaccine according to any one of [1] to [6], wherein the hepatitis B vaccine composition is prepared with a gel base material comprising carboxy vinyl polymer that is treated by adding an outside shearing force to add spray-performance which is to control that (1) as for the particle-size-distribution of the sprayed composition, the mean particle size is in a range of 40 μm to 70 μm, and the particle distribution between 10 μm and 100 μm is 90% or more,
    (2) the spray density is uniform to form a homogeneous full-cone shape, and
    (3) the spray angle is adjusted in a range of 40° to 60°.

[9] The rhinovaccination system of hepatitis B vaccine according to any one of [2] to [8], wherein the nozzle orifice includes substantially no curved portion.

[10] The rhinovaccination system of hepatitis B vaccine according to any one of [2] to [9], wherein the tip portion defining the nozzle orifice has thickness along an injection direction of the formulation which is in a range between 0.20 mm and 0.30 mm.

[11] The rhinovaccination system of hepatitis B vaccine according to any one of [2] to [10],
    wherein the nozzle body includes an inner wall having at least a portion formed in a cylindrical shape and the packing rod includes an outer wall at least a portion formed in a cylindrical shape having a plurality of circumferentially spaced grooves,
    wherein the nozzle chamber is defined between the at least portion of the inner wall of the nozzle body and the at least portion of the outer wall of the packing rod, and
    wherein the packing rod includes a vortex-flow generation member opposed to the tip portion of the nozzle body.

[12] The rhinovaccination system of hepatitis B vaccine according to [11], wherein the vortex-flow generation member is formed so that a flow direction of the formulation from the grooves of the packing rod is offset to a central axis, thereby to generate a vortex flow of the formulation.

[13] The rhinovaccination system of hepatitis B vaccine according to [11] or [12], wherein the at least portion of the inner wall of the nozzle body is formed to have a cross section substantially-perpendicular to the injection direction which is continuously or step-wisely reduced towards the injection direction.

[14] The rhinovaccination system of hepatitis B vaccine according to any one of [1] to [13], for preventing and/or treating hepatitis B.

[15] A method for preventing and/or treating hepatitis B, comprising administering the hepatitis B vaccine composition to a patient in need thereof with the rhinovaccination system of hepatitis B vaccine according to any one of [1] to [13].

[16] The rhinovaccination system of hepatitis B vaccine according to any one of [1] to [13], for use in preventing and/or treating hepatitis B.

Effect of the Invention

The present invention have made it possible to provide a nosal hepatitis B vaccine composition comprising hepatitis B surface antigen (HBs antigen) and hepatitis B nucleocapsid antigen (HBc antigen) as an active ingredient, but not needing an adjuvant, which induces a high immune response in spite of a small antigen level, and low side effects because the composition does not comprise an adjuvant. By using an administration system equipped with a metered-dose syringe-based squirt having an optimized-shaped rhinal spray nozzle, the hepatitis B vaccine composition is expected to be suitably applied for treating and preventing hepatitis B.

The hepatitis B vaccine composition for nasal administration of the present invention can be broadly spread, attached, and retained for a long time in nasal mucosa because the composition comprises a gel base material comprising carboxy vinyl polymer which is treated by adding an outside shearing force to add spray-performance, thus the hepatitis B vaccine composition of the present invention can induce a high immune response in spite of a small antigen level.

The hepatitis B vaccine composition for nasal administration of the present invention is expected to not only prevent but also treat hepatitis B by using an administration system equipped with the metered-dose syringe-based squirt having an optimized-shaped rhinal spray nozzle.

DESCRIPTION OF EMBODIMENTS

Figure 1:
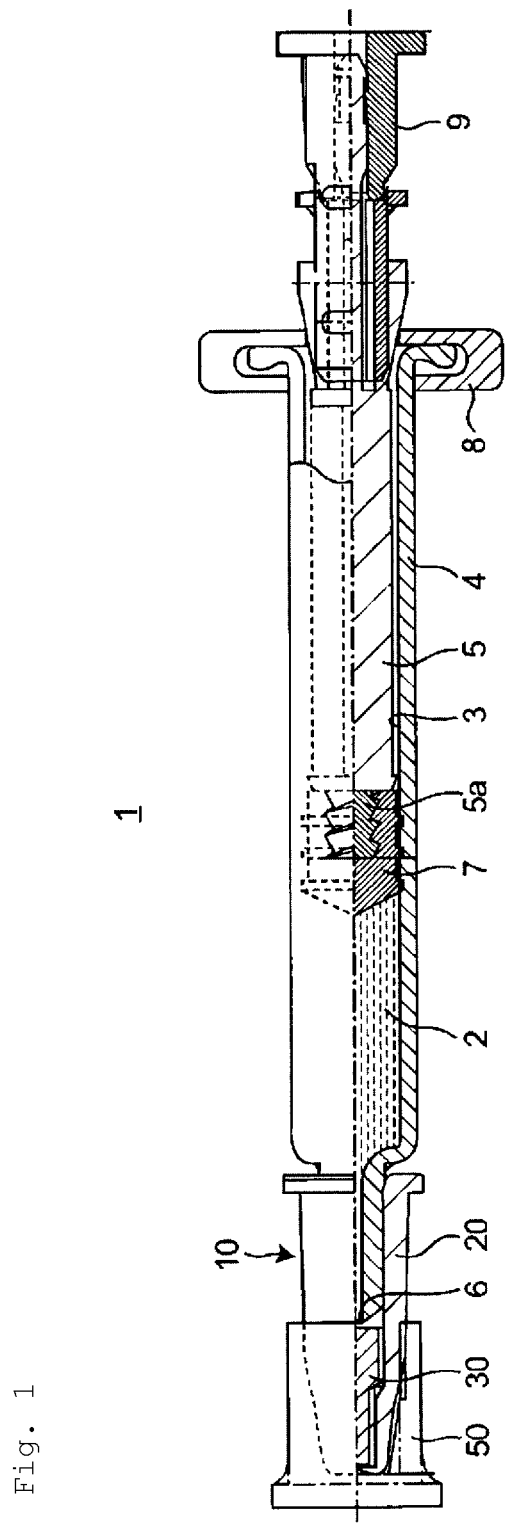
FIG. 1 is a partially-fragmented side view of a general structure of a medical syringe comprising a rhinal spray nozzle of one embodiment according to the present invention.

The present invention provides a rhinovaccination system of hepatitis B vaccine, comprising
 a medical syringe having a tip opening in fluid communication with a syringe barrel, which is equipped with a rhinal spray nozzle comprising a hollow nozzle body having a tip portion defining a nozzle orifice thereon, a solid packing rod arranged within the nozzle body, and a nozzle chamber defined between the packing rod and the nozzle body to allow a fluid communication between the tip opening and the nozzle orifice, wherein the nozzle orifice has a diameter in a range between 0.25 mm and 0.30 mm,
 which is filled with a nasal hepatitis B vaccine composition which comprises (i) a gel base material comprising carboxy vinyl polymer which is treated by adding an outside shearing force to add spray-performance, and (ii) hepatitis B surface antigen (HBs antigen) and hepatitis B nucleocapsid antigen (HBc antigen), which is characterized by not needing an adjuvant.

The "rhinovaccination system of hepatitis B vaccine" used herein means a combination of a vaccine composition and an administration device, that is, the present syringe-based squirt filled with the present hepatitis B vaccine composition.

The "gel base material comprising carboxy vinyl polymer which is treated by adding an outside shearing force to add spray-performance" used herein means, for example, a "gel base material comprising a skin/mucosa-adhesive agent" disclosed in WO 2007/123193, which is a base material comprising carboxy vinyl polymer and optionally comprising gellan gum, whose viscosity is adjusted by adding an outside shearing force. The actual outside shearing force disclosed in WO 2007/123193 is not a simple stirring or shaking, i.e., the operation giving the shearing force herein can be carried out with a device known by a skilled person, for example, a high-speed spinning-type emulsifying device, a colloidal mill-type emulsifying device, a high-pressure emulsifying device, a roll mill-type emulsifying device, an ultrasonic-type emulsifying device and a membrane-type emulsifying device can be used as a device giving shearing force. Especially, a homo mixer-type, a comb-type, and an intermittently-jet-stream-generating-type, high-speed spinning-type emulsifying devices are preferable. The base material is characterized in that the viscosity thereof can be adjusted to various ones by adding an outside shearing force, and the spray spreading-angle from a spray container and the spray density can be controlled to meet the purpose. In addition, the use of the present rhinovaccination system equipped with a metered-dose syringe-based squirt having an optimized-shaped rhinal spray nozzle can achieve a good spray-suitability of a formulation (spray-dispersibility, uniformity of formulation particle size, etc.), as is the case with the pump-type spray device such as an airless-type spray device disclosed in WO 2007/123193, and thereby the use can make the spreading of hepatitis B antigen particles in nasal mucosa in a wide spread and in a long time to enhance the immunogenicity of the vaccine.

Carboxy vinyl polymer which is a material ingredient of the gel base material in the present invention is a hydrophilic polymer prepared by polymerizing acrylic acid as a main ingredient. To the gel base material, any ingredients can be added which can be chosen from pharmaceutical additives that are generally used to prepare an aqueous gel agent without any limitation.

The content of the gel base material comprising carboxy vinyl polymer which is treated by adding an outside shearing force to add spray-performance is 0.1-1.0 w/v %, preferably 0.3-0.7 w/v % as the content of carboxy vinyl polymer.

The vaccine of the present invention is characterized by comprising hepatitis B surface antigen (HBs antigen) and hepatitis B nucleocapsid antigen (HBc antigen) as an antigen. The hepatitis B antigen used herein means hepatitis B surface antigen and hepatitis B nucleocapsid antigen which are prepared in yeast by recombinant DNA technology.

As the above-mentioned hepatitis B antigen, a virus stock solution thereof is used herein, which is purified or concentrated to be mixed with the gel base material for spray-administration to nasal mucosa. With regard to the vaccine of the present invention, the concentration of each hepatitis B virus antigen is preferably 0.01-10 mg/mL, more preferably 0.05-5 mg/mL.

Hepatitis B surface antigen (HBs antigen) takes a particle form (diameter: about 50-60 nm) wherein there are a lot of antigenic proteins on the lipid membrane. The antigenic proteins are composed of originally three domains (S, Pre-S1, Pre-S2). The antigenic proteins are distinguished as follows: the antigen having all the three domains is HBsAg L-protein, the antigen lacking Pre-S1 is HBsAg M-protein, and the antigen lacking Pre-S1 and Pre-S2 is HBsAg S-protein. All the antigens can be prepared by using recombinant yeast.

An adjuvant is a generic term of substances having the modulating-activity of the immune response such as enhancement and suppression, and is used as an immunopotentiating agent to be added to a vaccine to enhance the immunogenicity of an antigen. Until now, a lot of adjuvants have been studied. The use of an adjuvant enhances the immune effect of a vaccine, but it has disadvantages of side effects such as inflammation. Some adjuvants can be chosen as a candidate to be used in a vaccine for nasal administration, but there has not been any approved vaccine for nasal administration comprising an adjuvant because there has been no adjuvant having a pervasive safety.

The present inventors have found that it is possible to prepare a vaccine having a high efficacy and low side effects in spite of non-adjuvant and a lower antigen level, which is not required to be in conjunction with another administration such as subcutaneous vaccination, when the gel base material which has the above-mentioned useful spray-performance such as high adhesive property to nasal mucosa is used with the above-mentioned hepatitis B vaccine. In addition, the present inventors have also found that using a device which can spray even a gel base material having high viscosity, hepatitis B vaccine composition can be sprayed to nasal mucosa, wherein the mean particle size of the sprayed composition is in a suitable range of 50 μm to 120 μm (preferably a range of 70 μm to 100 μm), the particle-size-distribution between 10 μm and 100 μm is 50% or more (preferably, 60% or more), the spray angle from the device is set at a range of 30° to 70° (preferably, a range of 40° to 60°) so that the composition can be administered to the desired site in nasal cavity, and the spray density is uniform to form a homogeneous full-cone shape. Further the present inventors have also found its process and a method for preventing and treating hepatitis B using the composition. Based upon the new findings, the present invention has been accomplished.

The "full-cone shape" which is used to express unbiased and uniform spray density is one of sprayed shape patterns, and the full-cone shape means homogeneous whole circle. The opposite word is "hollow cone" which has a doughnut shape.

The vaccine of the present invention can comprise an additional pharmaceutically-acceptable carrier(s) besides hepatitis B virus antigens and a gel base material for spray-administration to nasal mucosa. The carrier used herein can be a carrier which is generally used in the preparation of a vaccine or a formulation for administration in nasal cavity, which includes, for example, saline, buffered saline, dextrose, water, glycerin, isotonic aqueous buffer solution, and a combination thereof. And, the vaccine of the present invention may optionally include a preservative (e.g. thimerosal), an isotonic agent, a pH regulator, a surfactant, a stabilizing agent (e.g. disodium edetate hydrate), and an inactivating agent (e.g. formalin).

The vaccine of the present invention is used for spray-administration into the nasal cavity.

The vaccine of the present invention can prevent or treat hepatitis B.

For the administration of the vaccine, the spray is done to one or both nares with an optimized nose-spray nozzle of the present invention, which can be used as a disposable device.

The dosage of the vaccine should be decided considering the age, sex and weight of a patient or other factors, and the concentration of each hepatitis B virus antigen is preferably 0.01-10 mg/mL, more preferably 0.05-5 mg/mL. The amount of each antigen to be administered is preferably 0.1-5 mg/mL, more preferably 0.5-2 mg/mL.

With reference to attached drawings, embodiments of a rhinal spray nozzle used for a metered-dose syringe-based squirt having the rhinal spray nozzle according to the present invention will be described hereinafter. In the following description, directional terms such as "front", "rear", "proximal" and "distal" are conveniently used for better understandings, however, those terms are not intended to limit the scope of the present invention. Also, like components are denoted by like reference signs throughout the attached drawings.

(Medical Syringe)

FIG. 1 is a partially-fragmented side view of medical syringe 1 comprising rhinal spray nozzle 10 of an embodiment according to the present invention. As illustrated in FIG. 1, medical syringe 1 generally comprises syringe body 4 made of synthetic resin or glass having syringe barrel 3 capable of storing a pharmaceutical formulation therein, and plunger rod 5 inserted within syringe barrel 3 of syringe body 4. Medical syringe 1 also comprises piston 7 having fixing member 5a provided at the distal end of plunger rod 5 and sliding within syringe barrel 3 so as to pump the formulation in syringe barrel 3 out of distal tip opening 6 of syringe body 4, finger flange 8 provided around a proximal end of syringe body 4, and plunger end member 9 transmitting the force applied by a practitioner such as a medical doctor to plunger rod 5. Medical syringe 1 may be similar to the metered-dose syringe-based squirt disclosed in WO 2013/145789.

It should be noted that rhinal spray nozzle 10 of the present invention may be applicable to any type of medical syringes 1 which pump the formulation in syringe barrel 3 by pushing plunger rod 5 (and piston 7), and thus, the present invention will not be limited to the known configurations of the medical syringe. Therefore, the present disclosure will eliminate further description for the detailed structure of medical syringe (or metered-dose syringe-based squirt) 1, and discuss in more detail about the structure and the function of rhinal spray nozzle 10 used for the medical syringe. It should be noted that the disclosure of WO 2013/145789 is incorporated herein by reference into the present application.

(Rhinal Spray Nozzle)

Figure 2:
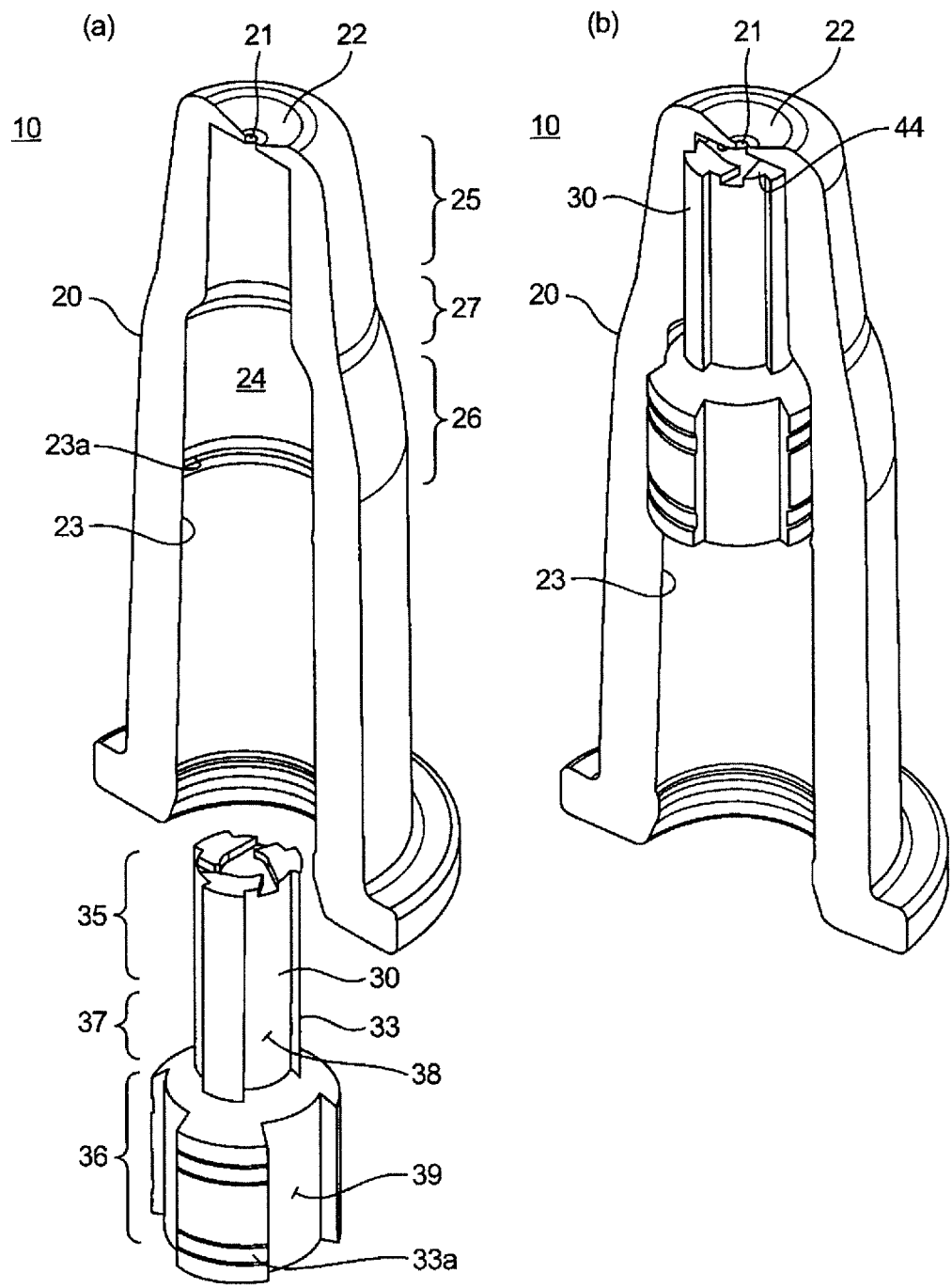
FIGS. 2(a) and 2(b) are partially-fragmented perspective views of the general structure of the rhinal spray nozzle of one embodiment of the present invention, showing configurations before and after the packing rod are inserted within the nozzle body, respectively.

As shown in FIG. 1, medical syringes 1 further comprises rhinal spray nozzle 10 opposed to tip opening 6 of syringe body 4, and protection cap 50 for protecting sterilized tip portion 22 of rhinal spray nozzle 10 from contaminant and mechanical impact. FIGS. 2(a) and 2(b) are partially-fragmented perspective views, showing the general structure of rhinal spray nozzle 10 of an embodiment of the present invention. As shown, rhinal spray nozzle 10 generally comprises hollow nozzle body 20 having tip portion 22 with nozzle orifice 21 and solid packing rod (packing bar) 30 provided within nozzle body 20. FIGS. 2(a) and 2(b) show rhinal spray nozzle 10 before and after packing rod 30 is arranged or inserted within nozzle body 20, respectively. Tip portion 22 of nozzle body 20 has a circular shape and is provided with nozzle orifice 21 at the center thereof.

Figure 3:
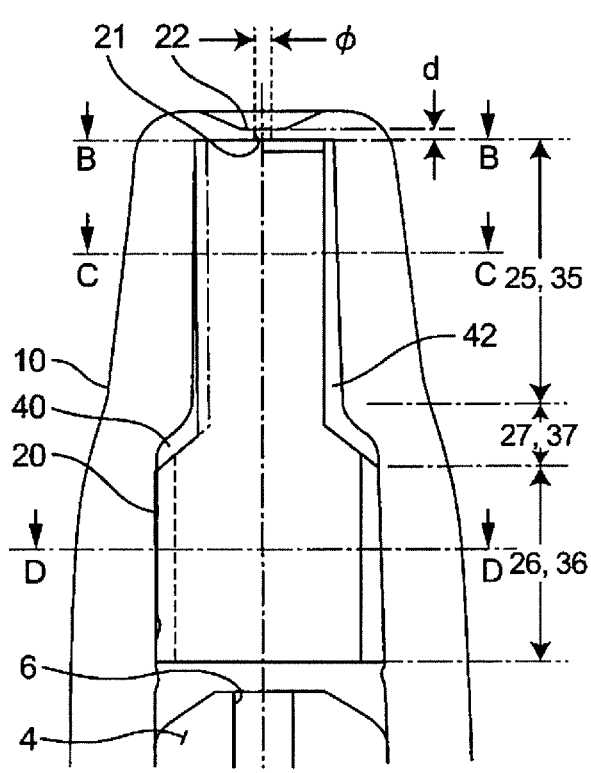
FIG. 3(a) is a vertical cross-sectional view of the rhinal spray nozzle of FIG. 2(b), and FIGS. 3(b), 3(c) and 3(d) are horizontal cross-sectional views of the rhinal spray nozzle taken along B-B line, C-C line and D-D line of FIG. 3(a), respectively.
Figure 3:
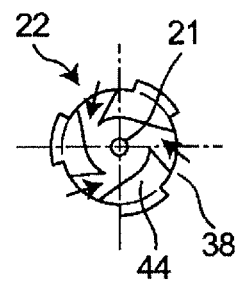
Figure 3:
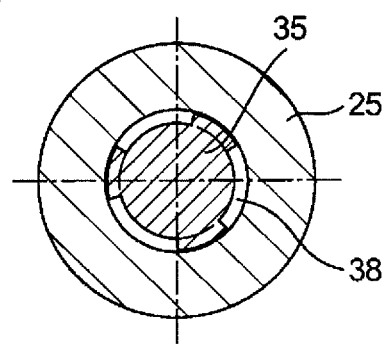
Figure 3:
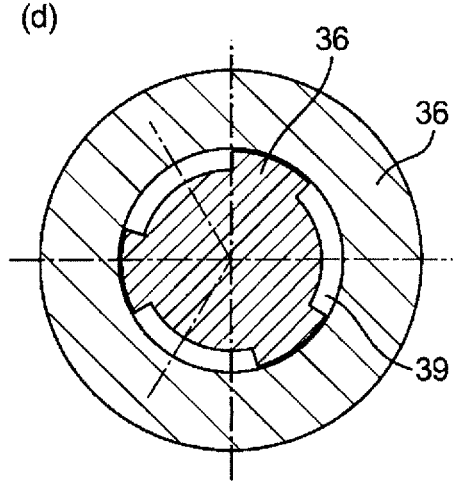
Figure 4:
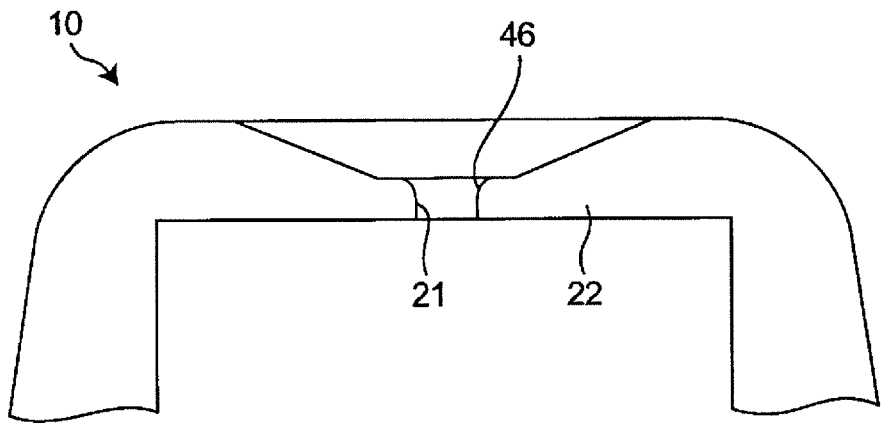
FIGS. 4(a) and 4(b) are enlarged cross-sectional views of the tip portion of the nozzle body, in which the tip portion is provided with the curved portion in FIG. 4(a) but not in FIG. 4(b).
Figure 4:
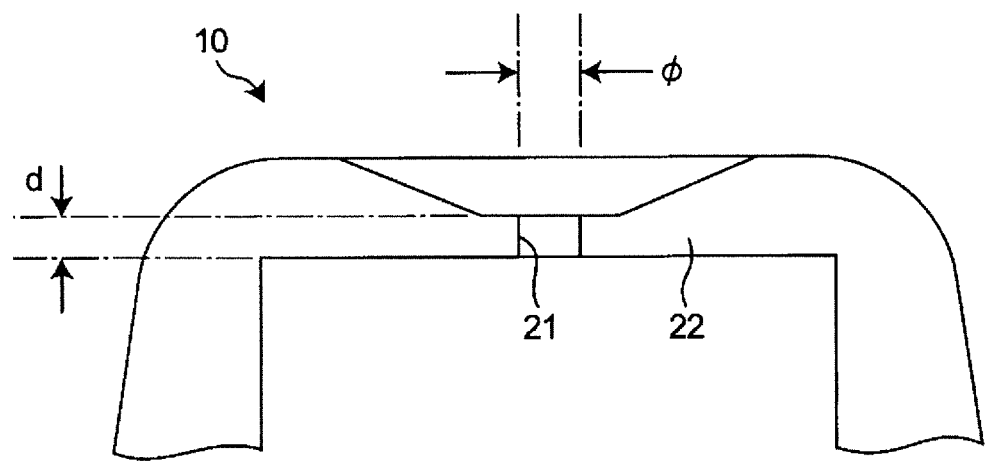
Figure 5:
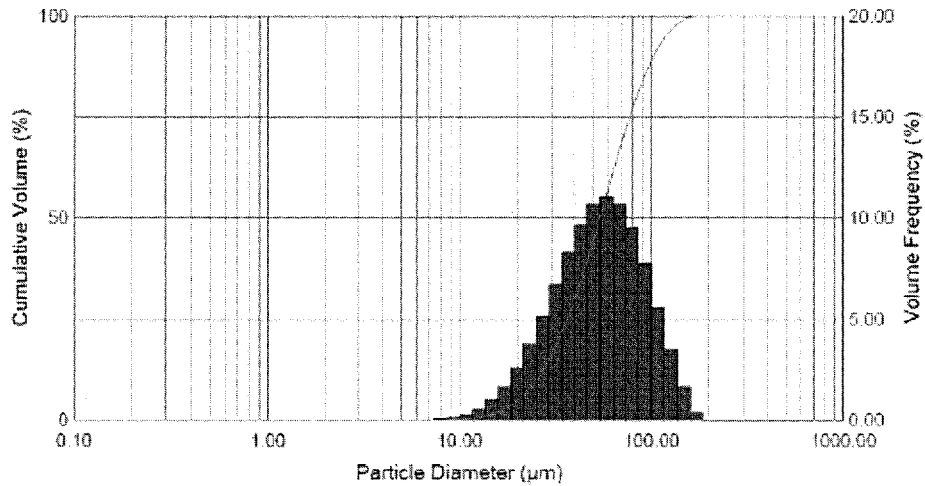
FIG. 5 shows a result that the particle size distribution of the formulation in Example 4 was measured with a laser diffraction particle size analyzer, which was sprayed with the syringe-based squirt of the present invention.
Figure 6:
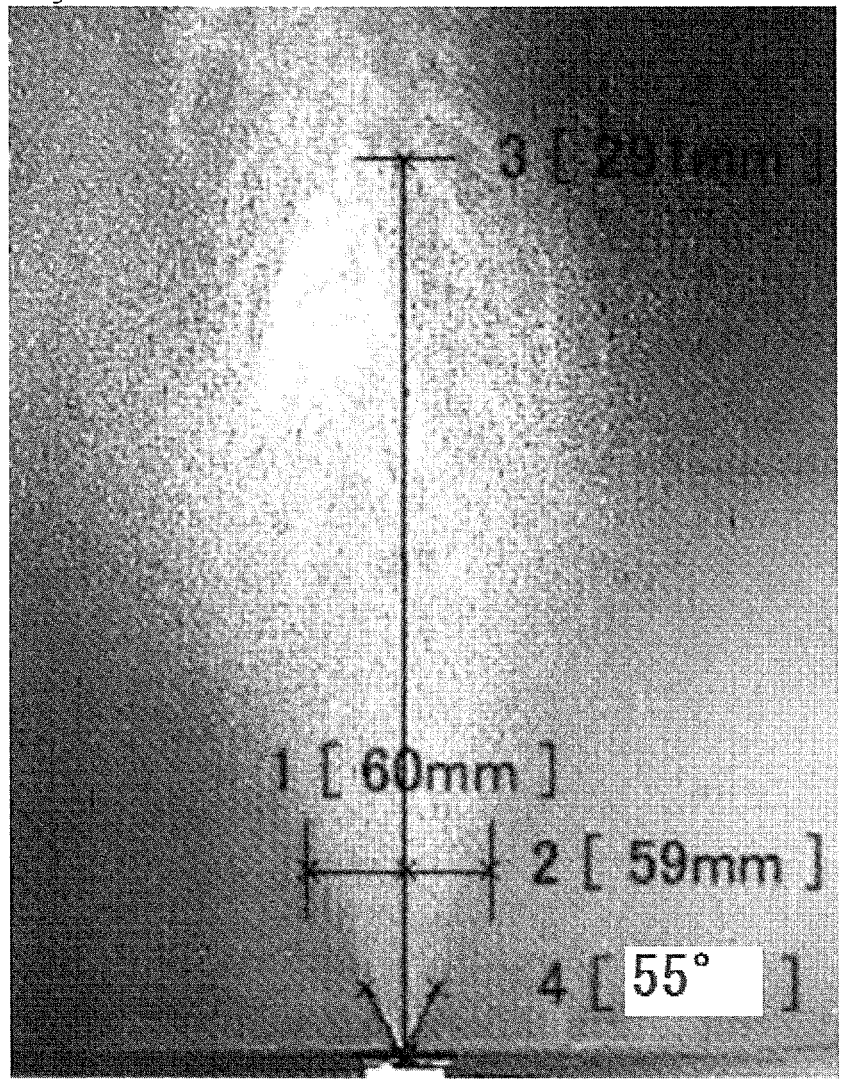
FIG. 6 shows a result that the spray angle of the formulation in Example 4 was measured with a high-speed microscope, which was sprayed from the tip of the nozzle in the syringe-based squirt of the present invention. The spray angle of the sprayed formulation was 52.27°.
Figure 7:
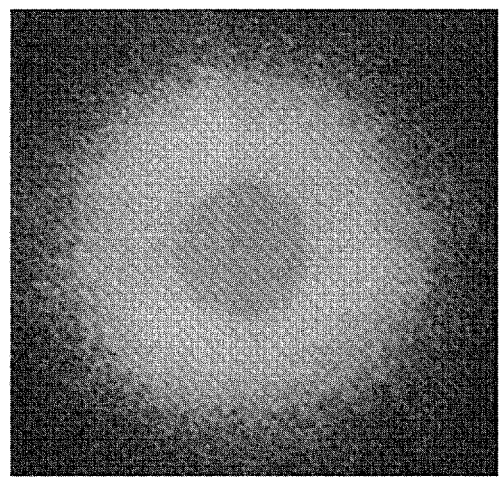
FIG. 7 shows a result that the spray behavior of the formulation in Example 4 was measured with a spray pattern test sheet, which was sprayed with the syringe-based squirt of the present invention. It was a uniform full-cone circle.

FIG. 3(a) is a vertical cross-sectional view of rhinal spray nozzle 10 of FIG. 2(b). FIGS. 3(b), 3(c) and 3(d) are horizontal cross-sectional views of rhinal spray nozzle 10 taken along B-B line, C-C line and D-D line of FIG. 3(a), respectively. Hollow nozzle body 20 defines internal space 24 of a substantially cylindrical shape. As shown in FIGS. 3(c) and 3(d), internal space 24 includes nozzle small-diameter portion 25 closer to nozzle orifice 21 of hollow nozzle body 20, nozzle large-diameter portion 26 opposing to tip opening 6 of syringe body 4, and nozzle shoulder 27 which is designed to have a diameter continuously or step-wisely reducing from nozzle large-diameter portion 26 towards nozzle small-diameter portion 25.

On the other hand, solid packing rod 30 to be inserted within nozzle body 20 has outer wall 33 having a configuration substantially complementary with inner wall 23 of nozzle body 20 (internal space 24). As shown in FIGS. 2(a), 3(c) and 3(d), rod small-diameter portion 35 and rod large-diameter portion 36 include rod shoulder 37 which is designed to have a diameter continuously or step-wisely reducing from rod large-diameter portion 36 towards rod small-diameter portion 35.

Preferably, as illustrated in FIG. 3(a), inner wall 23 of nozzle body 20 is provided with protrusion 23a, while outer wall 33 of packing rod 30 is provided with recess 33a for receiving protrusion 23a. When packing rod 30 is fully inserted within internal space 24 of nozzle body 20, protrusion 23a may be closely fit in recess 33a to ensure connection between packing rod 30 and nozzle body 20.

Also as illustrated in FIGS. 2(a)-2(b) and 3(a)-3(d), packing rod 30 includes a plurality of grooves 38 and 39 circumferentially spaced from one another both on rod small-diameter portion 35 and rod large-diameter portion 36. Also, packing rod 30 is inserted within nozzle body 20 so as to define gap 40 between nozzle shoulder 27 and rod shoulder 37 (FIG. 3(a)). Thus, rhinal spray nozzle 10 assembled as illustrated in FIG. 2(b) has nozzle chamber 42 defined by grooves 38, 39 and gap 40, which allows fluid communication of formulation 2 delivered from tip opening 6 of syringe body 4 through nozzle chamber 42 to tip portion 22 of rhinal spray nozzle 10.

Furthermore, as shown in FIG. 3(b), packing rod 30 includes vortex-flow generation member 44 opposed to tip portion 22 of rhinal spray nozzle 10. Vortex-flow generation member 44 is configured to generate a vortex flow of formulation 2 that is delivered from each of grooves 38 of rod small-diameter portion 35 before being injected from nozzle orifice 21 of nozzle body 20. More particularly, the end portions of rod small-diameter portion 35 which define vortex-flow generation member 44 are formed so as to extend offset the vertical central axis of nozzle orifice 21. Thanks to generation of the vortex flow of formulation 2 before being injected from nozzle orifice 21, the spray angle of formulation 2 can be expanded to spray it in a more uniform manner.

As illustrated in FIGS. 3(c)-3(d), it is preferable to design grooves 38 of rod small-diameter portion 35 to be less than grooves 39 of rod large-diameter portion 36 so as to increase the pressure of formulation 2 in vortex-flow generation member 44 before being injected from nozzle orifice 21. Also, thanks to the diameters of rod large-diameter portion 36 and rod small-diameter portion 35 which are designed to continuously or step-wisely be reduced from the former to the latter, it is easier to insert rhinal spray nozzle 10 deeply into the nasal cavity and to spray the formulation towards the inferior nasal concha and even deeper portions of the patient. Thus preferably, the diameter of rod small-diameter portion 35 is smaller enough than the nasal cavity opening of the patient without minimizing fear of the patient.

EXAMPLES

Hereinafter, the invention is illustrated based on examples, but are not limited thereto.

According to the methods shown below, gel base materials for spray-administration and hepatitis B virus stock solutions were prepared, and each gel base material and each virus stock solution were mixed as shown below to prepare hepatitis B vaccine compositions for administration to nasal mucosa.

<Preparation of Gel Base Material>
Example of Gel Base Material for Spray-Administration (1)

| Ingredients | Amount | Process of Preparation |
|---|---|---|
| Carboxy vinyl polymer | 11.0 mg | Each ingredient shown in the left column was mixed in the ratio corresponding to each weight shown there, and stirred to become homogeneous. Then, the mixture was given an outside shearing force by a high-speed rotation with an intermittently-jet-stream-generating-type high-speed spinning-type emulsifying device. The resulting base material whose viscosity was suitably adjusted with an outside shearing force was heated at 90° C. for 20 minutes to give a gel base material. Aspect: a clear and colorless gel base material, almost odorless. pH: 7.29 Viscosity: 3,800 mPa · s |
| L-Arginine | 24.0 mg | |
| Concentrated glycerin | 20.0 mg | |
| Purified water | q.s. | |
| Total | 1.0 mL | |

Example of Gel Base Material for Spray-Administration (2)

| Ingredients | Amount | Process of Preparation |
|---|---|---|
| Carboxy vinyl polymer | 30.0 mg | Each ingredient shown in the left column was mixed in the ratio corresponding to each weight shown there, and stirred to become homogeneous. Then, the mixture was given an outside shearing force by a high-speed rotation with an intermittently-jet-stream-generating-type high-speed spinning-type emulsifying device. The resulting base material whose viscosity was suitably adjusted with an outside shearing force was heated at 90° C. for 20 minutes to give a gel base material. Aspect: a clear and colorless gel base material, almost odorless. pH: 6.32 Viscosity: 21,230 mPa · s |
| L-Arginine | 55.0 mg | |
| Concentrated glycerin | 50.0 mg | |
| Purified water | q.s. | |
| Total | 1.0 mL | |

<Preparation of Virus Stock Solution Comprising Hepatitis B Virus Antigen>
Example of Virus Stock Solution (1)

| Ingredients | Amount |
|---|---|
| HBs antigen | 0.2 mg |
| HBc antigen | 0.2 mg |
| Sodium chloride | 7.9 mg |
| Disodium hydrogenphosphate ($Na_2HPO_4$) | 1.12 mg |
| Sodium dihydrogenphosphate dihydrate ($Na_2HPO_4 \cdot 2H_2O$) | 1.25 mg |
| Disodium edetate hydrate | 2.23 mg |
| Purified water | Total 1 mL |

Example of Virus Stock Solution (2)

| Ingredients | Amount |
|---|---|
| HBs antigen | 0.1 mg |
| HBc antigen | 0.1 mg |
| Sodium chloride | 7.9 mg |
| Disodium hydrogenphosphate ($Na_2HPO_4$) | 1.12 mg |
| Sodium dihydrogenphosphate dihydrate ($Na_2HPO_4 \cdot 2H_2O$) | 1.25 mg |
| Disodium edetate hydrate | 2.23 mg |
| Purified water | Total 1 mL |

<Mixture of Gel Base Material and Virus Stock Solution>

Example of gel base material (1) and Example of virus stock solution (1) mentioned above were mixed in the ratio of 1:1 under stirring to give a homogeneous hepatitis B vaccine composition for administration to nasal mucosa (Example 1). In the same way, Example of gel base material (2) and Example of virus stock solution (2) mentioned above were mixed in the ratio of 2:8 under stirring to give a homogeneous hepatitis B vaccine composition for administration to nasal mucosa (Example 2). The mixing under stirring can be completed softly and in a short time without giving a stress such as heat and pressure to the hepatitis B vaccine antigen. The quantities of each ingredient in the resulting hepatitis B vaccine composition for administration to nasal mucosa, the physical properties thereof, and the spray-performances thereof derived by spraying the compositions with a suitable device are also shown below.

Example 1

| Ingredients | Amount | Physical property/spray-performance |
|---|---|---|
| HBs antigen | 0.1 mg | pH: 7.15 |
| HBc antigen | 0.1 mg | Viscosity: 517 mPa · s |
| Carboxy vinyl polymer | 5.50 mg | Spray-performance in spraying 250 µL of the |
| L-Arginine | 12.00 mg | solution with a spray |
| Concentrated glycerin | 25.00 mg | device which has no pump |
| Sodium chloride | 3.95 mg | function: |
| Disodium hydrogenphosphate ($Na_2HPO_4$) | 0.56 mg | Mean particle size of sprayed formulation: 55.9 µm |
| Sodium dihydrogenphosphate dihydrate ($Na_2HPO_4 \cdot 2H_2O$) | 0.625 mg | Ratio of particle size between 10 µm and 100 µm: 87.3% |
| Disodium edetate hydrate | 1.115 mg | Spray angle from the device: 53° |
| Purified water | q.s. | Spray density: full-cone |
| Total | 1.0 mL | uniformly-circle |

Example 2

| Ingredients | Amount | Physical property/spray-performance |
|---|---|---|
| HBs antigen | 0.08 mg | pH: 6.39 |
| HBc antigen | 0.08 mg | Viscosity: 407 mPa · s |
| Carboxy vinyl polymer | 6.00 mg | Spray-performance in spraying 250 µL of the |
| L-Arginine | 11.00 mg | solution with a spray |
| Concentrated glycerin | 10.00 mg | device which has no pump |
| Sodium chloride | 6.32 mg | function: |
| Disodium hydrogenphosphate ($Na_2HPO_4$) | 0.896 mg | Mean particle size of sprayed formulation: 59.7 µm |
| Sodium dihydrogenphosphate dihydrate ($Na_2HPO_4 \cdot 2H_2O$) | 1.00 mg | Ratio of particle size between 10 µm and 100 µm: 88.8% |
| Disodium edetate hydrate | 1.784 mg | Spray angle from the device: 55° |
| Purified water | q.s. | Spray density: full-cone |
| Total | 1.0 mL | uniformly-circle |

Thus, by filling a medical syringe having a tip opening in fluid communication with a syringe barrel, which is equipped with a rhinal spray nozzle comprising a hollow nozzle body having a tip portion defining a nozzle orifice thereon, a solid packing rod arranged within the nozzle body, and a nozzle chamber defined between the packing rod and the nozzle body to allow a fluid communication between the tip opening and the nozzle orifice, wherein the nozzle orifice has a diameter in a range between 0.25 mm and 0.30 mm with the formulation for nasally-administering hepatitis B vaccine of Example 2 which was prepared with a gel base material prepared by adding an outside shearing force, a rhinovaccination system of the hepatitis B vaccine having spray-performance which is to control that (1) as for the particle-size-distribution of the sprayed composition, the mean particle size is in a range of 30 µm to 80 µm [59.7 µm], and the particle distribution between 10 µm and 100 µm is 80% or more [88.8%], (2) the spray density is uniform to form a homogeneous full-cone shape, and (3) the spray angle is adjusted in a range of 30° to 70° [55°] was able to be prepared.

Efficacy of Prevention and Treatment in Human Clinical Test
(Subject)

As for the evaluation of preventive efficacy, the subjects thereof were beforehand tested about immune response with subcutaneous and intramuscular inoculation vaccine and divided to the following three groups: (1) vaccine non-responders who were not antibody-induced, (2) vaccine responders who were antibody-induced, and (3) unvaccinated people as control. As for the evaluation of therapeutic efficacy, the subjects thereof were divided to the following two groups: (4) asymptomatic carriers with HBV-emia who did not develop hepatitis, and (5) CHB patients in NA treatment.

<Evaluation of Preventive Efficacy>

The hepatitis B vaccine composition for administration to nasal mucosa which was prepared in Example 2 was administered to each group's subject by transnasal spray with a syringe-based squirt equipped with a rhinal spray nozzle in an amount of 0.5 mL for one nostril (in total, 1.0 mL for both nostrils). The (1) vaccine non-responders, the (2) vaccine responders, and the (3) unvaccinated people received the nasal administration once in two weeks, in total three times.

(Efficacy to Vaccine Non-Responders for Subcutaneous and Intramuscular Inoculation)

To 13 vaccine non-responders who had no immune response to subcutaneous and intramuscular inoculation, the nasal administration of vaccine was carried out three times. One month after the final administration, the HBs antibody titer and HBc antibody titer were measured. The antibody level of HBs and HBc in all the 13 people increased (Table 1).

TABLE 1

Efficacy to vaccine non-responders for subcutaneous and intramuscular inoculation

| Subject | Antibody level of HBs (mIU/mL) | | Antibody level of HBc (S/CO) | |
|---|---|---|---|---|
| | pre | post | pre | post |
| vaccine non-responder 1 | 0 | ≥500* | 0.2 | 15.8 |
| vaccine non-responder 2 | 0 | ≥500* | 0.1 | 1.8 |
| vaccine non-responder 3 | 0 | ≥500* | 0.1 | 11.2 |
| vaccine non-responder 4 | 0 | 141 | 0.1 | 22.9 |
| vaccine non-responder 5 | 0 | 263 | 0.1 | 33.7 |
| vaccine non-responder 6 | 4.4 | ≥500* | 0.1 | 7.7 |
| vaccine non-responder 7 | 3.2 | 39.7 | 0.1 | 2.4 |
| vaccine non-responder 8 | 6.1 | ≥500* | 0.1 | 4.5 |
| vaccine non-responder 9 | 0 | 27.3 | 0.1 | 0.2 |
| vaccine non-responder 10 | 3.1 | 308 | 0.1 | 25.3 |
| vaccine non-responder 11 | 0 | 25.2 | 0.1 | 0.9 |
| vaccine non-responder 12 | 0 | ≥500* | 0.1 | 12.6 |
| vaccine non-responder 13 | 8 | ≥500* | 0.1 | 16.8 |

≥500*: off-scale high (Efficacy to Vaccine Responders for Subcutaneous and Intramuscular Inoculation)

To 19 vaccine responders, the nasal administration of vaccine was carried out three times. One month after the final administration, the HBs antibody titer and HBc antibody titer were measured. In all the 19 people, the antibody level of HBs went above the measurement sensitivity (i.e., off-scale high), and the antibody level of HBc increased (Table 2).

TABLE 2

Efficacy to vaccine responders for subcutaneous and intramuscular inoculation

| Subject | Antibody level of HBs (mIU/mL) | | Antibody level of HBc (S/CO) | |
|---|---|---|---|---|
| | pre | post | pre | post |
| vaccine responder 1 | 62.4 | ≥500* | 0.2 | 15 |
| vaccine responder 2 | 110.0 | ≥500* | 0.1 | 2.5 |
| vaccine responder 3 | 62 | ≥500* | 0.1 | 4 |
| vaccine responder 4 | 11.6 | ≥500* | 0.2 | 14.2 |
| vaccine responder 5 | 14.1 | ≥500* | 0.1 | 1.1 |
| vaccine responder 6 | 42 | ≥500* | 0.1 | 19.2 |
| vaccine responder 7 | 61.7 | ≥500* | 0.1 | 3.1 |
| vaccine responder 8 | 35.5 | ≥500* | 0.1 | 10.1 |
| vaccine responder 9 | 10.9 | ≥500* | 0.1 | 13.1 |
| vaccine responder 10 | 57.9 | ≥500* | 0.1 | 1.4 |
| vaccine responder 11 | 36.9 | ≥500* | 0.1 | 59 |
| vaccine responder 12 | 44.1 | ≥500* | 0.1 | 7.4 |
| vaccine responder 13 | 53.3 | ≥500* | 0.1 | 21 |
| vaccine responder 14 | 17.1 | ≥500* | 0.1 | 15.7 |
| vaccine responder 15 | 30 | ≥500* | 0.1 | 2.7 |
| vaccine responder 16 | 52.1 | ≥500* | 0.1 | 41.9 |
| vaccine responder 17 | 37.2 | ≥500* | 0.1 | 34.5 |
| vaccine responder 18 | 22.3 | ≥500* | 0.1 | 28 |
| vaccine responder 19 | 15 | ≥500* | 0.1 | 38.4 |

≥500*: off-scale high (Efficacy to Unvaccinated People)

To 7 unvaccinated people, the nasal administration of vaccine was carried out three times. One month after the final administration, the HBs antibody titer and HBc antibody titer were measured. The antibody level of HBs and HBc in 6 people increased (Table 3).

TABLE 3

Efficacy to unvaccinated people

| Subject | Antibody level of HBs (mIU/mL) | | Antibody level of HBc (S/CO) | |
|---|---|---|---|---|
| | pre | post | pre | post |
| unvaccinated person 1 | 0 | 157 | 0.1 | 14.8 |
| unvaccinated person 2 | 0 | 332 | 0.1 | 0.8 |
| unvaccinated person 3 | 0 | 19.1 | 0.1 | 6.5 |
| unvaccinated person 4 | 0 | 0 | 0.1 | 2.8 |
| unvaccinated person 5 | 0 | 4.6 | 0.1 | 0.1 |
| unvaccinated person 6 | 0 | 12.7 | 0.1 | 10.9 |
| unvaccinated person 7 | 0 | 51.9 | 0.1 | 121 |

<Evaluation of Therapeutic Efficacy>

The hepatitis B vaccine composition for administration to nasal mucosa which was prepared in Example 2 was administered to each group's subject by transnasal spray with a syringe-based squirt equipped with a rhinal spray nozzle in an amount of 0.5 mL for one nostril (in total, 1.0 mL for both nostrils). The (4) asymptomatic carriers and the (5) CHB patients in NA treatment received the nasal administration once in two weeks, in total ten times.

(Efficacy to Asymptomatic Carriers)

To 41 asymptomatic carriers, the nasal administration of vaccine was carried out ten times. Before the administration, and 6 months after the final administration, HBV-DNA level, the change rate of HBs antigen level, and the positive conversion ratio of HBs antibody were evaluated. Six months after the final administration, the HBV-DNA level did not obviously change, but the HBs antigen level decreased to 78.6% from 100% of the before-administration. In 20 examples of the total 41 ones, the HBs antibody increased, thus the positive conversion ratio was 48.8% (Table 4).

TABLE 4

Evaluation of therapeutic efficacy to asymptomatic carriers

| | Residual ratio of HBV-DNA level (%) | Residual ratio of HBs antigen level (%) | Positive conversion ratio of HBs antibody (%) |
|---|---|---|---|
| asymptomatic carriers | no obvious change | 78.6 | 48.8 |

(CHB Patients in NA Treatment)

To 29 CHB patients in NA treatment, the nasal administration of vaccine was carried out ten times. Six months after the final administration, HBV-DNA level, the change rate of HBs antigen level, and the positive conversion ratio of HBs antibody were evaluated.

The HBV-DNA level evaluated before the administration was lower than the detective level in all patients because the patients were in NA treatment, and the level evaluated months after the final administration still remained lower than the detective level. The HBs antigen level was 79.3% for 100% of the before-administration. In 11 examples of the total 29 ones, the HBs antibody increased, thus the positive conversion ratio was 37.9% (Table 5).

TABLE 5

Evaluation of therapeutic efficacy to CHB patients in NA treatment

| | Residual ratio of HBV-DNA level (%) | Residual ratio of HBs antigen level (%) | Positive conversion ratio of HBs antibody (%) |
|---|---|---|---|
| CHB patients in NA treatment | lower than detective level and without change | 79.3 | 37.9 |

DENOTATION OF REFERENCE NUMERALS

1: medical syringe, 2: pharmaceutical formulation, 3: syringe barrel, 4: syringe body, 5: plunger rod, 5a: fixing member, 6: opening, 7: piston, 8: finger flange, 9: plunger end member, 10: rhinal spray nozzle, 20: nozzle body, 21: nozzle orifice, 22: tip portion, 23: inner wall, 23a: protrusion, 24: internal space, 25: nozzle small-diameter portion, 26: nozzle large-diameter portion, 27: nozzle shoulder, 30: packing rod, 33: outer wall, 33a: recess, 35: rod small-diameter portion, 36: rod large-diameter portion, 37: rod shoulder, 38, 39: groove, 40: gap, 42: nozzle chamber, 44: vortex-flow generation member, 46: curved portion, 50: protection cap.

The invention claimed is:

1. A rhinovaccination system of hepatitis B vaccine, comprising a syringe-based squirt filled with a hepatitis B vaccine composition which comprises (i) hepatitis B surface antigen (HBs antigen) and/or hepatitis B nucleocapsid antigen (HBc antigen), and (ii) a gel base material comprising carboxy vinyl polymer which is treated by adding an outside shearing force to add spray-performance.

2. The rhinovaccination system of hepatitis B vaccine according to claim 1, wherein the syringe-based squirt is a medical syringe having a tip opening in fluid communication with a syringe barrel, which is equipped with a rhinal spray nozzle comprising
a hollow nozzle body having a tip portion defining a nozzle orifice thereon,
a solid packing rod arranged within the nozzle body, and
a nozzle chamber defined between the packing rod and the nozzle body to allow a fluid communication between the tip opening and the nozzle orifice,
wherein the nozzle orifice has a diameter in a range between 0.25 mm and 0.30 mm.

3. The rhinovaccination system of hepatitis B vaccine according to claim 1, wherein the amount of (i) the hepatitis B vaccine is 0.01-10 mg/mL per each antigen.

4. The rhinovaccination system of hepatitis B vaccine according to claim 1, wherein the hepatitis B vaccine composition comprises 0.1 w/v % to 1.0 w/v % carboxy vinyl polymer.

5. The rhinovaccination system of hepatitis B vaccine according to claim 1, wherein the spray-performance is to control (1) the particle-size-distribution of the sprayed composition, (2) the uniformity of spray density, and/or (3) the spray angle.

6. The rhinovaccination system of hepatitis B vaccine according to claim 1, wherein the hepatitis B vaccine composition is prepared by treating a gel base material comprising 0.5 w/v % to 2.0 w/v % carboxy vinyl polymer by adding an outside shearing force to control (1) the particle-size-distribution of the sprayed composition, (2) the uniformity of spray density, and/or (3) the spray angle, as spray-performance, to give a gel base material, and then
mixing the resulting gel base material with a virus stock solution comprising hepatitis B surface antigen (HBs antigen) and/or hepatitis B nucleocapsid antigen (HBc antigen) homogeneously in a short time without stress.

7. The rhinovaccination system of hepatitis B vaccine according to claim 1, wherein the hepatitis B vaccine composition is prepared with a gel base material comprising carboxy vinyl polymer that is treated by adding an outside shearing force to add spray-performance which is to control that (1) as for the particle-size-distribution of the sprayed composition, the mean particle size is in a range of 30 μm to 80 μm, and the particle distribution between 10 μm and 100 μm is 80% or more,
(2) the spray density is uniform to form a homogeneous full-corn shape, and
(3) the spray angle is adjusted in a range of 30° to 70°.

8. The rhinovaccination system of hepatitis B vaccine according to claim 1, wherein the hepatitis B vaccine composition is prepared with a gel base material comprising carboxy vinyl polymer that is treated by adding an outside shearing force to add spray-performance which is to control that (1) as for the particle-size-distribution of the sprayed composition, the mean particle size is in a range of 40 μm to 70 μm, and the particle distribution between 10 μm and 100 μm is 90% or more,
(2) the spray density is uniform to form a homogeneous full-corn shape, and
(3) the spray angle is adjusted in a range of 40° to 60°.

9. The rhinovaccination system of hepatitis B vaccine according to claim 2, wherein the nozzle orifice includes substantially no curved portion.

10. The rhinovaccination system of hepatitis B vaccine according to claim 2, wherein the tip portion defining the nozzle orifice has thickness along an injection direction of the formulation which is in a range between 0.20 mm and 0.30 mm.

11. The rhinovaccination system of hepatitis B vaccine according to claim 2,
wherein the nozzle body includes an inner wall having at least a portion formed in a cylindrical shape and the packing rod includes an outer wall at least a portion formed in a cylindrical shape having a plurality of circumferentially spaced grooves,
wherein the nozzle chamber is defined between the at least portion of the inner wall of the nozzle body and the at least portion of the outer wall of the packing rod, and
wherein the packing rod includes a vortex-flow generation member opposed to the tip portion of the nozzle body.

12. The rhinovaccination system of hepatitis B vaccine according to claim 11, wherein the vortex-flow generation member is formed so that a flow direction of the formulation from the grooves of the packing rod is offset to a central axis, thereby to generate a vortex flow of the formulation.

13. The rhinovaccination system of hepatitis B vaccine according to claim 11, wherein the at least portion of the inner wall of the nozzle body is formed to have a cross section substantially-perpendicular to the injection direction which is continuously or step-wisely reduced towards the injection direction.

14. The rhinovaccination system of hepatitis B vaccine according to claim 1, for preventing and/or treating hepatitis B.

15. A method for preventing and/or treating hepatitis B, comprising administering the hepatitis B vaccine composition to a patient in need thereof with the rhinovaccination system of hepatitis B vaccine according to claim 1.

16. The rhinovaccination system of hepatitis B vaccine according to claim 1, for use in preventing and/or treating hepatitis B.

* * * * *